(12) United States Patent
Bernard et al.

(10) Patent No.: US 9,162,965 B2
(45) Date of Patent: Oct. 20, 2015

(54) METHOD FOR PRODUCING A LACTIC ESTER FROM A FERMENTATION JUICE CONTAINING AMMONIUM LACTATE

(75) Inventors: Aurélie Bernard, Escanaffles (BE); Pierre-Antoine Mariage, Escanaffles (BE); Jean-Christophe Bogaert, Escanaffles (BE)

(73) Assignee: GALACTIC S.A., Escanaffles (BE)

( * ) Notice: Subject to any disclaimer, the term of this patent is extended or adjusted under 35 U.S.C. 154(b) by 157 days.

(21) Appl. No.: 13/882,129

(22) PCT Filed: Oct. 17, 2011

(86) PCT No.: PCT/EP2011/068066
§ 371 (c)(1),
(2), (4) Date: Jun. 24, 2013

(87) PCT Pub. No.: WO2012/055717
PCT Pub. Date: May 3, 2012

(65) Prior Publication Data
US 2013/0274505 A1    Oct. 17, 2013

(30) Foreign Application Priority Data
Oct. 28, 2010    (BE) .................................. 2010/0639

(51) Int. Cl.
C07C 67/20 (2006.01)
C07C 67/08 (2006.01)
B01D 3/00 (2006.01)

(52) U.S. Cl.
CPC ................ *C07C 67/20* (2013.01); *B01D 3/009* (2013.01); *C07C 67/08* (2013.01)

(58) Field of Classification Search
CPC ......... B01D 3/009; C07C 67/08; C07C 67/20

USPC .......................................................... 560/179
See application file for complete search history.

(56) References Cited

U.S. PATENT DOCUMENTS

| | | | |
|---|---|---|---|
| 2,565,487 A | | 8/1951 | Filachione et al. |
| 5,814,498 A | * | 9/1998 | Mani et al. .................... 435/136 |
| 2003/0029711 A1 | | 2/2003 | Cockrem et al. |
| 2006/0231378 A1 | * | 10/2006 | Wolfgang et al. ............. 202/176 |
| 2009/0137825 A1 | * | 5/2009 | Bauduin et al. ............... 549/263 |

FOREIGN PATENT DOCUMENTS

| | | | |
|---|---|---|---|
| CN | 1930110 | * | 3/2007 |
| EP | 0 614 983 A2 | | 9/1994 |
| EP | 0 517 571 B1 | | 1/1996 |
| WO | WO 2006/069113 A2 | | 6/2006 |
| WO | WO 2007/013259 A1 | | 2/2007 |

OTHER PUBLICATIONS

English translation of CN1930110, Mar. 14, 2007.*
Noronha et al., "Recovery of lactic acid by batch reactive distillation," J. Chem. Technol. Biotechnol, 2006, 81, 1141-1150.*
European Patent Office, International Search Report in International Patent Application No. PCT/EP2011/068066 (Jan. 17, 2012).
Rakesh Kumar et al., "Esterification of Lactic Acid with n-Butanol by Reactive Distillation," Ind. Eng. Chem. Res., (2007) vol. 46, pp. 6873-6882.

* cited by examiner

*Primary Examiner* — Paul A Zucker
*Assistant Examiner* — Mark Luderer
(74) *Attorney, Agent, or Firm* — Leydig, Voit & Mayer, Ltd.

(57) ABSTRACT

The present invention relates to an industrial process for producing a lactic ester containing in total at least seven carbon atoms, from a fermentation liquor containing ammonium lactate in order to avoid the inherent production of gypsum, with a high yield and according to which the loss of lactic ester in the form of lactamide is limited as much as possible.

8 Claims, 1 Drawing Sheet

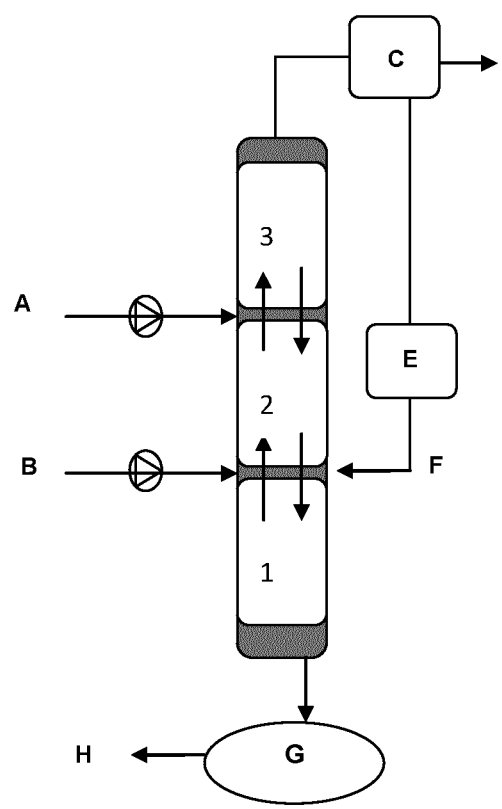

METHOD FOR PRODUCING A LACTIC ESTER FROM A FERMENTATION JUICE CONTAINING AMMONIUM LACTATE

CROSS-REFERENCE TO RELATED APPLICATIONS

This patent application is the U.S. national phase of International Application No. PCT/EP2011/068066, filed on Oct. 17, 2011, which claims the benefits of Belgium Patent Application No. 2010/0639, filed Oct. 28, 2010, the disclosures of which are incorporated by reference.

FIELD OF THE INVENTION

The present invention relates to an industrial method for producing a lactic acid without the simultaneous production of gypsum. In particular, the present invention relates to an industrial method for producing a lactic ester containing in total at least seven carbon atoms, from a fermentation juice containing ammonium lactate in order to avoid the inherent production of gypsum, with a high yield and according to which the loss of lactic ester in the form of lactamide is limited as much as possible.

PRIOR ART

The production of lactic acid by the conventional fermentation method is known, which consists of the transformation, by a microorganism, of a carbonaceous substance (glucose, sucrose, starch, cellulose, fructose, etc.) in the presence of calcium carbonate. The solution obtained is then treated by an acid in order to release the lactic acid in protonated form but this acidification step involves the production of calcium sulphate (also called gypsum). However, it is well known to persons skilled in the art that the formation of gypsum means that the precipitate must then be filtered while the lactic acid is purified and concentrated by techniques such as ion exchange resins, decoloration on charcoal, nanofiltration, evaporation, distillation or liquid/liquid extraction.

In addition, on an industrial scale, reprocessing of the gypsum becomes problematic because the quantities produced are large and the gypsum produced may be difficult to reprocess. It must be eliminated as a waste, giving rise to not insignificant costs and an impact on the environment. The production of lactic acid without gypsum is therefore of great interest.

In order to remedy this important drawback, it has already been proposed, as in the patent U.S. Pat. No. 2,565,487 or the patent WO 2007/013 259, to produce lactic acid esters from ammonium salts and more particularly ammonium lactate, and alcohol. The ester produced can, in a second step, be hydrolysed into lactic acid. These methods are not carried out continuously.

It is also known that, during fermentation, the lactic acid produced by the microorganisms can be neutralised with ammonia. The ammonium lactate thus formed can be esterified by means of alcohol in order to form the corresponding lactic ester.

However, it is also well known that the production method passing through ammonium salts also has many drawbacks, which make it in particular difficult to transpose a method using this pathway to an industrial scale.

This is because, when the fermentation juice is concentrated as well as during the esterification step, the formation of an undesirable by-product, lactamide, has been observed.

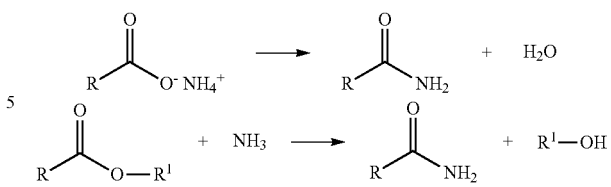

The formation of lactamide during the conversion of ammonium lactate into lactic ester reduces the selectivity of the reaction, causes a yield decrease and requires separation and an additional elimination.

As explained in the patent WO 2006/069 113, in order to avoid the formation of lactamide, it is necessary to work with a large molar excess of alcohol ranging from 20 to 100 moles of alcohol per mole of ammonium lactate. The purification of the ester formed by distillation of the alcohol in large excess consequently requires a large energy input incompatible with profitable industrial use of the method.

Moreover, when a lactic fermentation juice is used in the form of non-purified ammonium lactate, the concentration and esterification steps are made difficult by the precipitation of by-products of the fermentation (sugar residues, etc.). This precipitation gives rise to a low esterification yield.

Not only does the prior art make it possible to clearly know the problems relating to the presence of lactamide, but in addition the prior art also mentions the problem of the racemisation of the esters obtained from a lactic fermentation juice in the form of ammonium lactate, as described by M. Alas in the patent EP 517 571 B1, where the possibility of producing lactic esters with a racemisation rate greater than 2% is taught, which is well known to be detrimental for the ester obtained.

The article "Esterification of lactic acid with n-butanol by reactive distillation" (*Ind. Eng. Chem. Res.* 2007, 46, 6873-6882) mentions the production of lactic ester (hydrolysable to lactic acid) by esterification of lactic acid and not starting from a fermentation juice, and it therefore does not solve the problems related to lactamides and does not propose a complete method for fermentation as far as lactic acid.

There therefore exists a need for an industrial method for producing lactic acid without the conjoint production of gypsum and which remedies the drawbacks mentioned here above.

One of the objects of the present invention is related to a method that remedies these problems, starting from a fermentation juice in the form of ammonium lactate.

Another object of the invention is related to a method for obtaining a lactic acid without the formation of gypsum with high yield, generally >95%, and wherein the loss in the form of lactamide does not exceed 5% during the esterification step.

Yet another object of the invention is related to a method that limits the racemisation to a level below 2%.

BRIEF DESCRIPTION OF THE INVENTION

The applicant has now unexpectedly found that a lactic ester could be produced with a total number of carbon atoms greater than or equal to 7 from a flow of ammonium lactate with a yield greater than 95%, by subjecting, to reactive distillation, a flow of ammonium lactate coming from a purified and concentrated fermentation juice, in liquid form, conjointly with a flow of aliphatic alcohol with 4 to 8 carbon atoms, in vapour form, recovering at the base of the column a liquid flow of the corresponding lactic ester and at the head of the column a gaseous mixture comprising the alcohol in excess, the ammonia and the water.

DETAILED DESCRIPTION OF THE INVENTION

The applicant company has found a method for producing a lactic ester from a flow of ammonium lactate, not involving the production of gypsum and remedying the drawbacks mentioned here above concerning the production by way of ammonium salts.

The method of the invention comprises successively the following steps: first of all a pre-purification of a fermentation juice in the form of ammonium lactate is carried out; this pre-purified fermentation juice is then subjected to concentration and followed to a reactive distillation in the presence of a gaseous flow of an aliphatic alcohol containing 4 to 8 carbon atoms in order to effect the esterification of the ammonium lactate; these last two operations being performed in a single apparatus consisting of three levels; the ester thus produced is recovered and then purified by distillation.

1. Pre-purification of the Fermentation Juice

The applicant observed surprisingly that the various steps of the pre-purification afforded not only a reduction in the lactamide by-product but also in the racemisation rate.

The first step of the pre-purification consists of an elimination of the biomass by any techniques known to the person skilled in the art such as, non-limitatively, filtration on pre-layer, membrane filtration, settling or centrifugation. This step is followed by a decationisation of the fermentation juice on an ion exchange resin previously conditioned in ammoniacal form. The fermentation juice with its divalent cations removed is then treated by nanofiltration.

2. Concentration of the Pre-purified Fermentation Juice

The fermentation juice thus purified is next concentrated until a concentration of between 50% and 80% is obtained.

A preferred version of the present invention consists of using the techniques of evaporation on a thin film for this concentration step, which once again limits the formation of lactamide. Under these conditions, also no racemisation was observed during this step.

3. Esterification of the Ammonium Lactate

The esterification of the concentrated ammonium lactate is carried out in a flow in the opposite direction to an alcohol flow containing at least four carbon atoms, in gaseous form in an apparatus (FIG. 1) enabling good liquid/gas exchange. It has been found that residence times of less than 2 hours are perfectly suitable and that excellent results can even be obtained with residence times of less than 30 minutes. The apparatus used consists of a reactive distillation column with three levels so that:

a) The vapours leave level 1 (number of theoretical plates=20) through the head of level 1 into the foot of level 2 and the vapours leave level 2 (number of theoretical plates=15) through the head of level 2 into the foot of level 3 (number of theoretical plates=10).

b) The liquids from level 2 leave through the foot of level 2 into the head of level 1 and the liquids from level 3 leave through the foot of level 3 into the head of level 2.

c) The ammonium lactate with a concentration of between 10% and 80% is introduced into the head of level 2.

d) Alcohol with $C \geq 4$ in the form of vapour coming from the head of level 1 is introduced into the foot of level 2.

e) The lactic ester formed is recovered at the foot of level 1 with a lactamide content of less than 5%.

f) The gaseous mixture of alcohol ($C \geq 4$), water and ammonia is recovered at the head of level 3.

g) The alcohol ($C \geq 4$) is separated from the water and ammonia by decantation and is reintroduced into the foot of level 2.

The alcohol is heated to its boiling point (the temperature and pressure being dependent on the alcohol used) and introduced into the column at the foot of level 2 via the pipe B in FIG. 1, in the form of a gas. The previously pre-purified and concentrated solution of ammonium lactate, in which a catalyst, preferentially but not limitatively para-toluene sulphonic acid (PTSA) is optionally added so as to accelerate the reaction, is introduced into the head of level 2 via the pipe A in FIG. 1. The ascending alcohol vapours therefore flow in the opposite direction to the descending liquid flow of ammonium lactate. The water formed during esterification is entrained by the ascending alcohol vapours and recovered on the condenser C at the head of level 3 as set out in FIG. 1. The ammonia released during the reaction is also taken away and is found in this same aqueous phase.

The excess of alcohol also recovered on the condenser C is then separated from the aqueous phase containing the ammonia at C by settling and then heated and gasified in an exchanger E and reintroduced at F at the foot of level 2. The alcohol/ammonium lactate molar ratio is between 4:1 and 2:1, preferentially 3:1. In the case where the alcohol is butanol, the method may be conducted at a temperature of 120° C. and at atmospheric pressure.

The sizing of the stages of the column can easily be done by a person skilled in the art but, by way of non-limitative information, it can be considered that levels 1, 2 and 3 consist of a lining, structured or not, and contain respectively 20, 15 and 10 theoretical plates. In the context of the invention, these levels can also consist of bell plates or with any other column profile known to the person skilled in the art in order to promote the liquid/vapour exchanges.

This method enables the recovery, via the pipe H at the discharge from the boiler G in FIG. 1, of a lactic ester with a yield greater than 95%, wherein the lactamide loss is less than 5% and the racemisation less than 2%.

4. Purification of the Lactic Ester Produced

The lactic ester thus formed may if necessary be purified by any techniques known to the person skilled in the art, provided that this step does not lead to any new racemisation. The distillation residue may be recovered and recycled at the esterification step.

The purified lactic ester may where necessary be hydrolysed into lactic acid. It is in this case possible to achieve high-quality grades meeting market criteria.

Other details and particularities of the invention, given below by way of non-limitative examples, emerge from the description as a few possible embodiments thereof.

EXAMPLE 1

Esterification of the Ammonium Lactate in the Apparatus of the Invention

The fermentation juice was filtered on a dicalite pre-layer in order to eliminate the biomass. The filtrate was then treated on LEWATIT 2528 cationic resins preconditioned in ammonia form in order not to exceed 20 ppm in divalent cations. The flow rate was fixed at 2 BV/h (a BV or "bed volume" corresponds to the volume occupied by the resin bed in the treatment column).

This fermentation juice is next treated by nanofiltration, with a feed rate of between 500 and 600 ml/h, on an Osmonics SEPACF2 nanofiltration pilot with a GEWATER (DL) membrane.

Finally, the fermentation juice is concentrated, in a thin-layer apparatus, at a pressure of between 90 and 120 mbar and a temperature of 100° and 105° C. with a feed rate of 6 l/h, until a concentration of 60% is obtained.

A column corresponding to the diagram of FIG. 1 is supplied with butanol in vapour form at 120° C. at atmospheric pressure, at the head of level 1 (FIG. 1, position B) with a flow rate of 550 g/h. Level 1 consists of a structured lining and contains 20 theoretical plates. The boiler G at the foot of level 1 consists of a plate exchanger heated to 140° C. The pre-purified ammonium lactate concentrated at 60% is mixed with 1% PTSA in order to be introduced at the head of level 2 (FIG. 1, position A) with a flow rate of 1204 g/h. Level 2 contains the same structured lining as level 1 with a number of theoretical plates of 15. The water formed and the butanol are entrained at the head of level 3 (FIG. 1, position C). Level 3 is also composed of a structured lining and contains 10 theoretical plates. The aqueous phase containing the ammonia collected on the condenser at position C is then separated from the butanol by decantation. The butanol collected after decantation is for its part heated to boiling (FIG. 1, position E) in a heat exchanger and returned to the head of level 1 (FIG. 1, position F), in order to ensure equilibrium, with a flow rate of 1500 g/h. The butyl lactate is recovered at the foot of level 1 (FIG. 1, position H). Monitoring of the reaction as a function of time was carried out and the results are set out in table 1.

TABLE 1

Characteristics of the butyl lactate produced as a function of time

| Time (h) | Butyl lactate brought out (g/h) | Conc. of butyl lactate[a] (%) | Conc. of lactamide (%) | Conc. of water[b] (%) | Racemisation (%) | Loss of lactamide (%) | Yield (%) |
|---|---|---|---|---|---|---|---|
| 1 | 980.3 | 95 | 2 | 0.19 | 0 | 3.3 | 96 |
| 2 | 988.7 | 96 | 2 | 0.17 | 0 | 3.3 | 96 |
| 4 | 979.4 | 96.7 | 1.5 | 0.18 | 0 | 2.4 | 97 |
| 8 | 997.8 | 97 | 1 | 0.18 | 0 | 1.7 | 98 |
| 10 | 997 | 97 | 1.5 | 0.17 | 0 | 2.5 | 97 |
| 12 | 985.9 | 97.5 | 1 | 0.19 | 0 | 1.7 | 98 |

[a]Determined by gas chromatography measurement
[b]Determined by Karl Fisher measurement As shown by table 1, the apparatus makes it possible to produce butyl lactate from ammonium lactate in a stable manner (over 12 h) with a yield greater than 95%, a loss in the form of lactamide of less than 5% and a racemisation of less than 2%.

EXAMPLE 2

Esterification of a Pre-purified Fermentation Juice in Ammonium Lactate Form into Butyl Lactate with and without Use of a Column 222 g of butanol is placed in a flask and heated to 120° C. at atmospheric pressure, and 1% of PISA (para-toluene sulphonic acid) is added. When the butanol distils, 178.3 g of a pre-purified fermentation juice in the form of 60% ammonium lactate is added drop by drop into the flask. The reaction is continued until a zero residual acidity is obtained. At the end of synthesis, the reaction product is analysed and the results are set out in table 2.

TABLE 2

Characteristics of the butyl lactate produced

| Concentration of butyl lactate[a] (%) | Esterification yield (%) | Loss of lactamide (%) | Concentration of water[b] (%) | Racemisation (%) |
|---|---|---|---|---|
| 40.6 | 77 | 10 | 0.9 | 2 |

[a]Determined by gas chromatography measurement
[b]Determined by Karl Fisher measurement It can be noted that the conversion of the ammonium lactate into butyl lactate is not very high and that on the other hand the loss of lactamide is great.

A further test is carried out by surmounting the flask with a column containing a structured lining, in order to effect esterification flowing in the opposite direction to the alcohol in gaseous form.

222 g of butanol is placed in a flask surmounted by this column and heated to 120° C. at atmospheric pressure, and 1% of PTSA is added. When the butanol distils at the column head, 178.3 g of a pre-purified fermentation juice in the form of 60% ammonium lactate is added drop by drop at the column head. The reaction is continued until zero residual acidity is obtained. At the end of synthesis, the reaction product is analysed and the results are set out in table 3.

TABLE 3

Characteristics of the butyl lactate produced

| Concentration of butyl lactate (%) | Esterification yield (%) | Loss of lactamide (%) | Concentration of water (%) | Racemisation (%) |
|---|---|---|---|---|
| 50 | 96.2 | 4 | 0.18 | 0 |

Using a column makes it possible not only to increase the conversion of ammonium lactate into butyl lactate but also to reduce the loss of lactamide as well as the racemisation.

The butyl lactate produced is then purified by distillation and the characteristics are set out in table 4.

TABLE 4

Characteristics of the butyl lactate distilled

| Concentration of butyl lactate (%) | Distillation yield (%) | Loss of lactamides (%) | Concentration of water (%) | Racemisation (%) |
|---|---|---|---|---|
| 98 | 77 | 2 | 0.08 | 0 |

EXAMPLE 3

Concentration of Fermentation Juice with and without Pre-purification

Fermentation was carried out with ammonium neutralisation.

300 g of fermentation juice is directly concentrated in a flask. The characteristics of the concentrated fermentation juice in the form of ammonium lactate are set out in table 5.

TABLE 5

Characteristics of the fermentation juice after concentration

| Lactic acid[a] (g/l) | Lactamide[b] (ppm) | Yield (%) | Racemisation[c] (%) |
|---|---|---|---|
| 440 | 136,000 | 77 | 5 |

[a]Determined by titration
[b]Determined by HPLC measurement
[c]Determined by enzymatic analysis A significant formation of the lactamide by-product is observed during the concentration step.

A new fermentation was carried out with an ammonia neutralisation, this time the fermentation juice was filtered on a dicalite pre-layer in order to eliminate the biomass. The filtrate was next treated on LEWATIT 2528 cationic resins preconditioned in ammonia form in order not to exceed 20 ppm in divalent cations. The flow rate was fixed at 2 BV/h (a BV corresponds to the volume occupied by the resin bed in the treatment column).

This fermentation juice is next nanofiltered, with a feed rate of between 500 and 600 ml/h, on an Osmonics SEPACF2 nanofiltration pilot with a GEWATER (DL) membrane.

Finally, the fermentation juice is concentrated in a thin-layer apparatus at a pressure between 90 and 120 mbar and a temperature of between 100° and 105° C. with a feed rate of 6 l/h, until a concentration of 60% is obtained.

The characteristics of this fermentation juice in ammonium lactate form are set out in table 6.

TABLE 6

Characteristics of the pre-purified fermentation juice after concentration

| Total AL[a] (g/l) | Lactamide (ppm) | Yield (%) | Racemisation (%) |
|---|---|---|---|
| 540 | 3,400 | 99.4% | 1 |

[a]Ammonium lactate + lactic acid

It can be noted that the pre-purification on resin followed by a nanofiltration and concentration on a thin film considerably reduces the formation of lactamide and racemisation during concentration.

EXAMPLE 4

Esterification to 2-ethylhexyl Lactate of a Fermentation Juice in the Form of Ammonium Lactate 390 g of 2-ethylhexanol are placed in a flask surmounted by a column and heated to 130° C. at a pressure of 100 mbar, and 0.1% of PTSA is added. When the 2-ethylhexanol distils, 178.3 g of pre-purified ammonium lactate concentrated at 60% is added drop by drop at the column head. The reaction is continued until zero residual acidity is obtained. At the end of synthesis the reaction product is analysed and the results are set out in table 7.

TABLE 7

Characteristics of the 2-ethylhexyl lactate produced

| Concentration of 2-ethylhexyl lactate[a] (%) | Esterification Yield (%) | Loss of lactamide (%) | Concentration of water (%) | Racemisation (%) |
|---|---|---|---|---|
| 67 | 97 | 2 | 0.1 | 0.3 |

[a]Determined by gas chromatography

The 2-ethylhexyl lactate produced is then purified by distillation and the characteristics are set out in table 8.

TABLE 8

Characteristics of the distilled 2-ethylhexyl lactate

| Concentration of 2-ethylhexyl lactate (%) | Distillation efficiency (%) | Concentration of lactamide (%) | Concentration of water (%) | Racemisation (%) |
|---|---|---|---|---|
| 98 | 95 | 0.06 | 0.05 | 0.3 |

The very low concentration of lactamide and the equally low racemisation level can be noted.

EXAMPLE 5

Hydrolysis of the Butyl Lactate Produced in Example 2 into High-quality Lactic Acid 292 g of butyl lactate, 288 g of demineralised water and 1% of PTSA are placed in a flask and heated to 105° C. at atmospheric pressure. The reaction is continued for 8 hours. At the end of hydrolysis, the reaction product is analysed and the results are set out in table 9.

TABLE 9

Characteristics of the hydrolysed butyl lactate

| Concentration of butyl lactate (%) | Efficiency of hydrolysis (%) | Lactic acid (g/l) | Concentration of water (%) | Racemisation (%) |
|---|---|---|---|---|
| 0.6 | 99 | 510 | 0.08 | 0 |

99% of the butyl lactate was hydrolysed to lactic acid without causing racemisation of this lactic acid.

The lactic acid thus obtained is concentrated in order to meet the quality criterion for the market. The results are set out in table 10.

TABLE 10

Characteristics of the concentrated lactic acid

| Lactic acid (%) | Colouring (Hazen) | Racemisation (%) |
|---|---|---|
| 83.2 | 55 | 0 |

The invention claimed is:
1. A method of producing a lactic acid ester containing a total of at least 7 carbon atoms using a flow of ammonium lactate, wherein a reactive distillation is carried out in a col- umn of a flow of ammonium lactate, in liquid form, the ammonium lactate being pre-purified by
  a) elimination of biomass;
  b) decationization of fermentation juice on an ion exchange resin previously conditioned in ammoniacal form; and
  c) nanofiltration of the decationized juice;
  and concentrated simultaneously with a flow of aliphatic alcohol containing 4 to 8 carbon atoms, in vapor form, and wherein a corresponding liquid flow of lactic ester is recovered at the column foot and at the column head a gaseous mixture comprising aliphatic alcohol, ammonia and water.

2. The method according to claim 1, wherein the flow of pre-purified ammonium lactate is concentrated to a concentration level of between 50% and 80%.

3. The method according to claim 2, wherein the concentration is carried out by evaporation on thin film.

4. The method according to claim 1, wherein, during the reactive distillation, the molar ratio between the alcohol and the ammonium lactate is between 2:1 and 4:1.

5. The method according to claim 1, wherein, for the reactive distillation, the aliphatic alcohol is chosen among butanol, isoamyl alcohol and 2-ethylhexanol.

6. The method according to claim 1, wherein the distillation residue of the lactic acid produced is recovered and recycled at the esterification step.

7. The method according to claim 1, wherein the lactic ester containing at least 7 carbon atoms is hydrolyzed to lactic acid.

8. The method according to claim 7, wherein the alcohol issuing from the hydrolysis of the lactic ester containing at least 7 carbon atoms is recycled at the reactive esterification step.

* * * * *